(12) United States Patent
Casset et al.

(10) Patent No.: US 12,168,229 B2
(45) Date of Patent: Dec. 17, 2024

(54) DEVICE FOR LOCATING BIOLOGICAL OBJECTS

(71) Applicants: COMMISSARIAT A L'ENERGIE ATOMIQUE ET AUX ENERGIES ALTERNATIVES, Paris (FR); Institut National de la Sante et de la recherche Medicale, Paris (FR)

(72) Inventors: Fabrice Casset, Grenoble (FR); Arnaud Millet, Voreppe (FR); Baptiste Neff, Grenoble (FR)

(73) Assignees: COMMISSARIAT A L'ENERGIE ATOMIQUE ET AUX ENERGIES ALTERNATIVES, Paris (FR); Institut National de la Sante et de la recherche Medicale, Paris (FR)

( * ) Notice: Subject to any disclaimer, the term of this patent is extended or adjusted under 35 U.S.C. 154(b) by 370 days.

(21) Appl. No.: 16/953,601

(22) Filed: Nov. 20, 2020

(65) Prior Publication Data

US 2021/0154670 A1    May 27, 2021

(30) Foreign Application Priority Data

Nov. 21, 2019 (FR) .................................. 19 12994

(51) Int. Cl.
*B01L 3/00*    (2006.01)
*G01N 15/14*    (2006.01)
*G01N 15/149*    (2024.01)

(52) U.S. Cl.
CPC ........ *B01L 3/502761* (2013.01); *G01N 15/14* (2013.01); *B01L 2200/0647* (2013.01); *G01N 15/149* (2024.01)

(58) Field of Classification Search
None
See application file for complete search history.

(56) References Cited

U.S. PATENT DOCUMENTS

2012/0003709 A1    1/2012  Fukui et al.
2016/0244715 A1*   8/2016  Casset ................... C12M 23/20

FOREIGN PATENT DOCUMENTS

| EP | 1 734 110 A1 | 12/2006 |
| FR | 3 032 974 A1 | 8/2016 |
| FR | 3 043 093 A1 | 5/2017 |

OTHER PUBLICATIONS

French Preliminary Search Report issued Jul. 15, 2020 in French Application 19 12994 filed Nov. 21, 2019 (with English Translation of Categories of Cited Documents), 2 pages.

(Continued)

*Primary Examiner* — Rebecca M Giere
(74) *Attorney, Agent, or Firm* — Oblon, McClelland, Maier & Neustadt, L.L.P.

(57) ABSTRACT

Device for locating biological cells of at least one size, including a fluid cavity (3), fluid connection means (6.1, 6.2) configured to allow the introduction of liquid and cells into the fluid cavity, a plate (4) provided with an accommodating surface (8) having properties of adhesion vis-à-vis cells, said plate (4) being suspended in the fluid cavity (3), means (10) for vibrating the plate (4) in at least one stationary mode including at least one actuator (16) intended to act on the plate (4) and a control unit (UC) configured to control the at least one actuator so as to actuate the vibrating plate in a stationary mode at a wavelength greater than the size of the cells.

17 Claims, 5 Drawing Sheets

(56) References Cited

OTHER PUBLICATIONS

Neff, B. et al., "Development of a MEMS Plate Based on Thin-Film Piezoelectric AlN Actuators for Biological Applications," Proceedings, vol. 1, No. 386, doi: 10.3390, XP055714785, Aug. 9, 2017, 5 pages.
Casset, F. et al., "Low Voltage Actuated Plate for Haptic Applications With PZT Thin-Film," 2013 Transducers & Eurosensors XXVII: The 17th International Conference on Solid-State Sensors, Actuators and Microsystems, Barcelona, Spain, Jun. 16-20, 2013, 4 pages.
U.S. Appl. No. 15/335,702, filed Oct. 27, 2016, US 2017/0121661 A1, Fabrice Casset et al.
U.S. Appl. No. 16/335,511, filed Mar. 21, 2019, US 2020/0017354 A1, Fabrice Casset et al.
U.S. Appl. No. 16/475,901, filed Jul. 3, 2019, US 2019/0344278 A1, Vincent Agache et al.
U.S. Appl. No. 16/584,122, filed Sep. 26, 2019, US 2020/0106980 A1, Laurent Millet.
U.S. Appl. No. 16/921,117, filed Jul. 6, 2020, Stephane Fanget et al.

\* cited by examiner

DEVICE FOR LOCATING BIOLOGICAL OBJECTS

TECHNICAL FIELD AND PRIOR ART

The present invention relates to a device for locating biological objects on a surface, in particular with a view to studying cell migration.

Studying cell migration is a major challenge in studying cell behavior in a physiological or pathological context. One of the methods used for studying cell migration in vitro includes the production of one or more "scars" in a cell mat and analyzing the closure of the scar or scars. This closure is the direct result of the migration of the cells which are present. One of the techniques for forming the scar uses a stylus or a pipette, and the formation of the scar is therefore not well controlled and the level of reproducibility thereof is low. Another technique uses inserts, but the sizes available for the inserts and the need to bond them may interfere with the test. Other techniques use a chemical functionalization that makes it possible to study the interaction between the cells and their substrate but involves taking account of the chemistry used.

DESCRIPTION OF THE INVENTION

Consequently one aim of the present invention is to offer a device for locating biological objects on a surface in a controlled and repeatable manner.

The aim stated above is achieved by a cell-location device including a suspended plate, one face of which has adhesion properties with respect to the cells, means configured to actuate the plate in a stationary vibration mode at a wavelength greater than the size of the biological objects, for example the wavelength is greater than 400 µm.

The inventors found that the biological objects were distributed so as to form a zone devoid of any cell, for example in an antinode zone of the deflected shape of the plate actuated in a stationary mode.

This method therefore makes it possible to produce "scars" or exclusion zones in determined zones, i.e. for example the antinode zones, and with a width equal to approximately ¼ of the wavelength. Furthermore, these scars are repeatable, which makes it possible to carry out truly comparative studies between various cell populations.

The study of the migration of biological cells is therefore made more reliable.

In other words, using the generation of mechanical waves in a vibrating element causing the appearance of antinodes and troughs, the adhering objects are located spatially on the vibrating element. In the case of biological cells, this makes it possible to define exclusion zones of the cell adhesion in order to create for example "scars", which can then be invaded by the cells after stoppage of the vibrations and allow quantitative monitoring of the migration.

The cells are not "ejected" from the exclusion zone of the surface of the plate, but are located in the liquid before they are sedimented on the plate and adhere thereto, so as not to adhere in the sedimentation exclusion zone.

This device is advantageously compatible with the culture of mammal cells. This device is particularly adapted to the quantification of the impact of therapeutic molecules targeting the cytoskeleton for inhibiting metastatic invasion in cancer.

Advantageously, the device is at least partially optical transparent to enable cells to be observed during migration and to study the migratory behavior of the cells.

In a preferred embodiment, the plate is simply supported in the fluid cavity of the device, which allows the formation of scars of homogeneous width over the entire surface of the plate, avoiding the edge effects resulting from embedding.

One of the objects of the present application is a device for locating biological objects of at least a given size including a fluid cavity, fluid connection means configured to make it possible to introduce liquid and objects in the fluid cavity, a plate provided with an accommodating surface having properties of adhesion vis-à-vis the biological objects, said plate being suspended in the fluid cavity, means for vibrating the plate in at least one stationary mode including at least one actuator intended to act on the plate and a control unit configured to control the actuator so that the plate vibrates in a stationary mode of wavelength Λ lying between 3 times and 20 times the given size of the biological objects.

Another object of the present invention is a system for studying the migration of cells including a location device wherein at least part of the fluid cavity is optically transparent, and means for observing the biological objects on the plate.

Another object of the present application is a method for locating biological objects in a given pattern using a device according to the invention, including:
  placing liquid in the fluid cavity at least over part of the accommodating surface,
  injecting biological objects into said liquid,
  activating the at least one actuator so that the plate vibrates in a stationary mode chosen so as to obtain the given pattern,
  stopping the at least one actuator and sedimenting the biological objects on the accommodating surface in the given pattern.

BRIEF DESCRIPTION OF THE DRAWINGS

The present invention will be understood better on the basis of the following description and the accompanying drawings, on which.

DETAILED DISCLOSURE OF PARTICULAR EMBODIMENTS

The present invention is particularly adapted to the location of biological cells, the description will describe mainly the application to biological cells. However, the invention allows the location of any biological object able to adhere to the surface of a plate of the device. The size of the objects is between 1 μm and around a hundred μm.

For example, it may be a case of white corpuscles the size of which is approximately between 7 μm and 18 μm, circulating tumor cells the size of which is approximately 10 μm, red corpuscles the size of which is between 6 μm and 8 μm approximately, or bacteria the size of which is around 2 μm. The size of the adhering cells may range up to around a hundred micrometers.

The size of the objects is the largest dimension in the plane. When the object is substantially circular in shape, the size thereof corresponds to the diameter thereof, and when it is elongate in form, the size thereof corresponds to the dimension thereof in the elongate direction.

The device according to the invention, particularly in the production of scars, makes it possible to produce exclusion zones with a width greater than the size of a cell, preferably with a width equal to at least 100 μm, that is to say around 10 times the size of a cell.

Figure 1:
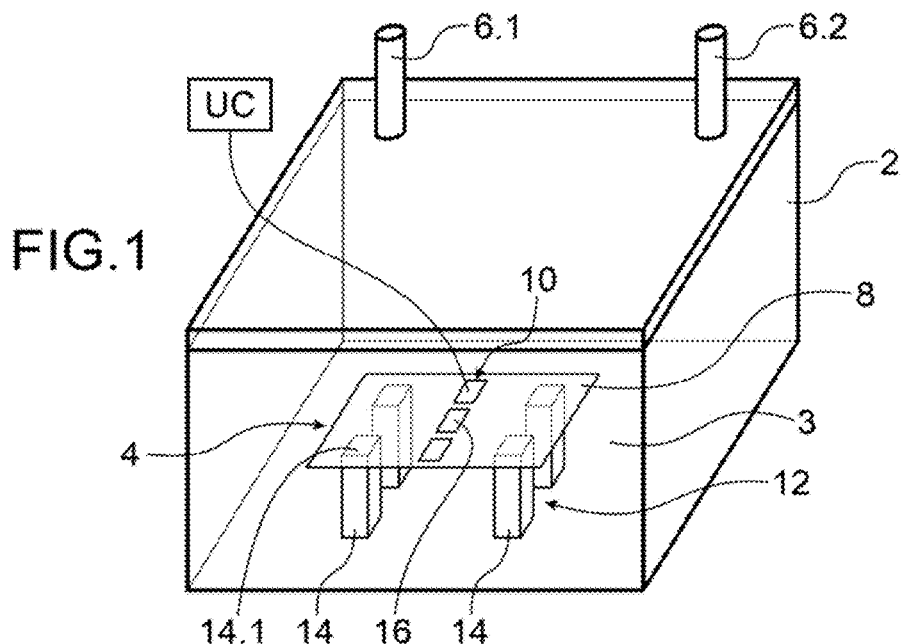
FIG. 1 is a schematic representation of a side view of an example of a cell-location device.

In FIG. 1, a schematic representation of a cell-location device can be seen.

Figure 9A:
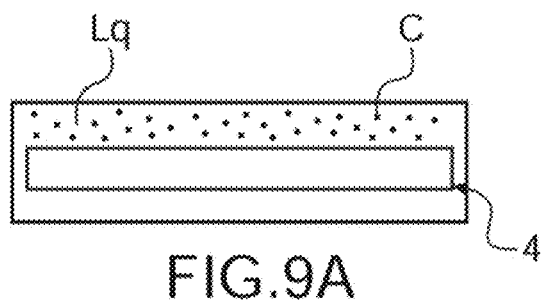
FIG. 9A is a schematic representation of the plate in a method for location by immersion.
Figure 9B:
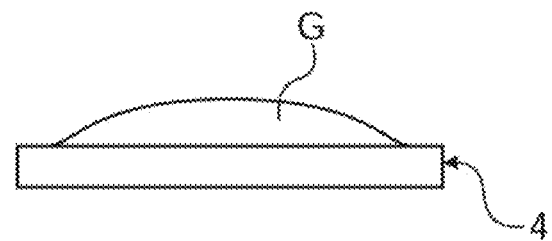
FIG. 9B is a schematic representation of the plate during a method for location by depositing a volume of liquid on the plate.

The device includes a housing 2 delimiting a fluid cavity 3, wherein a rectangular-shaped plate 4 is suspended, at least one entry for access to the interior of the housing either to supply liquid inside the housing and to immerse the plate (FIG. 9A), or to deposit liquid solely on the plate (FIG. 9B). In the example shown, the device includes a liquid-supply inlet 6.1 and a liquid-discharge outlet 6.2.

The plate 4 includes an accommodating face 8 on which the cells are intended to adhere.

The plate 4 has for example dimensions of between a few hundreds of μm and a few centimeters. The thickness of the plate is for example between 100 μm and a few mm.

The plate 4 is for example made from glass, silicon or any semiconductor material. The mechanical properties of the plate have an influence on the adhesion of the cells. An adhering cell creates a matrix of focal adhesions with the surface that is necessary for the organization of its cell architecture. The adhesion forces of the cells have values lying between around ten nanonewtons and around a hundred nanonewtons. These forces can be characterized by the use of an optical or magnetic clamp as well as by microplates.

The device also includes means 10 configured to vibrate the plate 4 in a stationary-wave mode having a wavelength greater than the size of the cells.

The plate actuated in a stationary mode will deform and exhibit zones moving with a maximum amplitude, designated "antinodes", and fixed zones designated "nodes". The nodes remain in the plane of the plate, the plane of the plate containing the plate at rest.

The means 10 include actuators able to exert an action on the plate in order to vibrate it.

In the example shown and preferably, the plate 4 is simply supported by a support structure 12 inside the housing. In the example shown, the support structure 12 includes columns 14 resting on the bottom of the housing and the plate is deposited on the free ends 14.1 of the columns. The "simply supported" connection makes it possible to obtain a more homogeneous deflected shape, as far as the edge of the plate.

Advantageously, the free ends 14.1 have a slightly adhesive treatment in order to hold the plate in the plane and prevent sliding of the plate.

The relative positioning of the columns 14 and of the plate 4 is chosen so that the contact between the columns and the plate takes place at vibration nodes, i.e. at the fixed zones. In the example shown, four columns are used.

The means 10 include actuators 16 for generating the vibration of the plate in a stationary mode. The actuators 16 are disposed with respect to the plate so as to be situated at at least one antinode of the deflected shape of the plate in the stationary mode to be actuated.

For example, the actuators are ferroelectric actuators, for example using PZT (lead zirconate titanate). In a variant the actuators are piezoelectric, electrostatic, magnetic or thermal actuators.

The actuators are fixed to the plate, for example on the face opposite to the accommodating face. In a variant, they are fixed to the accommodating face.

The actuators are controlled by a control unit UC, for example integrated in a computer, and including for example the operating conditions of the actuators so as to actuate the plate according to various modes according for example to the cells to be studied.

Figure 2A:
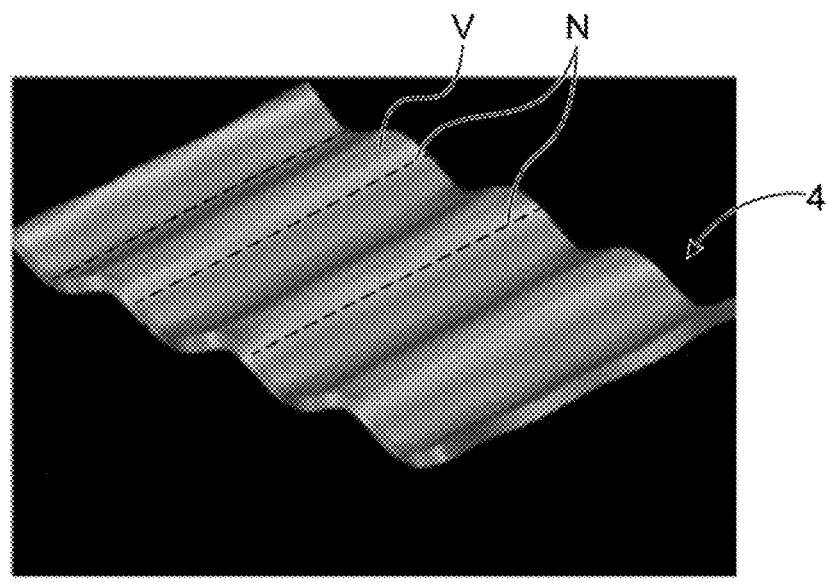
FIG. 2A is a perspective view of a plate used in the device of FIG. 1 actuated in a Lamb mode.

FIG. 2A shows a plate actuated in a Lamb mode, with the antinodes V and the nodes N. The actuators are distributed in the form of a band in the direction of the antinodes V. In this example the direction of the bands is the direction of the width of the plate.

Figure 2B:
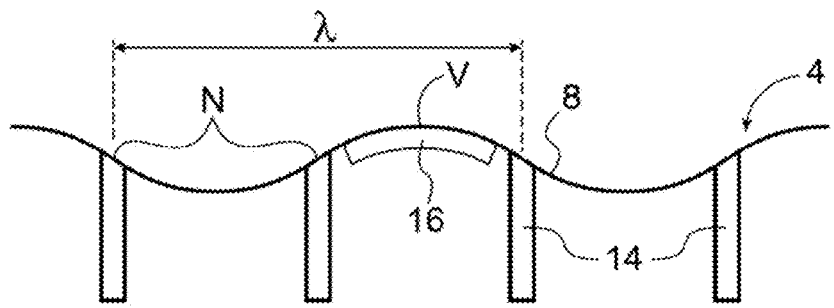
FIG. 2B is a side view of the plate in FIG. 2A.

In FIG. 2B there can be seen, in side view, the deflected shape of the plate 4 and the columns 14.

The wavelength of the deflected shape is designated X and covers one antinode and one trough. The wavelength of the stationary wave of the deflected shape of the plate is between 3 and 20 times the size of the cell, preferentially it is equal to 10 times the size of the cell. Preferably, the actuators have a width substantially equal to the size of an antinode.

The amplitude of the resonant mode is sufficient to move the liquid and therefore the cells in suspension therein. Typically the amplitude is between a few tens of nanometers and a few micrometers.

In one example, the means are adapted to actuate the plate using all the actuators so that the antinodes are always at the same locations.

In another advantageous example, the means 10 can activate all or some of the actuators, thus offering greater freedom in the choice of the actuation of the plate.

The location of the actuators and the size thereof can be determined using finite-element computing software, such as COMSOL®, ANSYS® or COVENTOR®, from the deflected shape in the vibration mode chosen. The resonant frequency of this mode and the amplitude can also be determined by finite-element simulation and/or by analytical calculation. The frequency and the amplitude are dependent on the voltage applied to the actuators.

The actuators can be determined as explained in the document Casset et al, *"Low voltage actuated plate for haptic applications with PZT thin-film"*, Proceedings of Transducers 2013.

Figure 5:
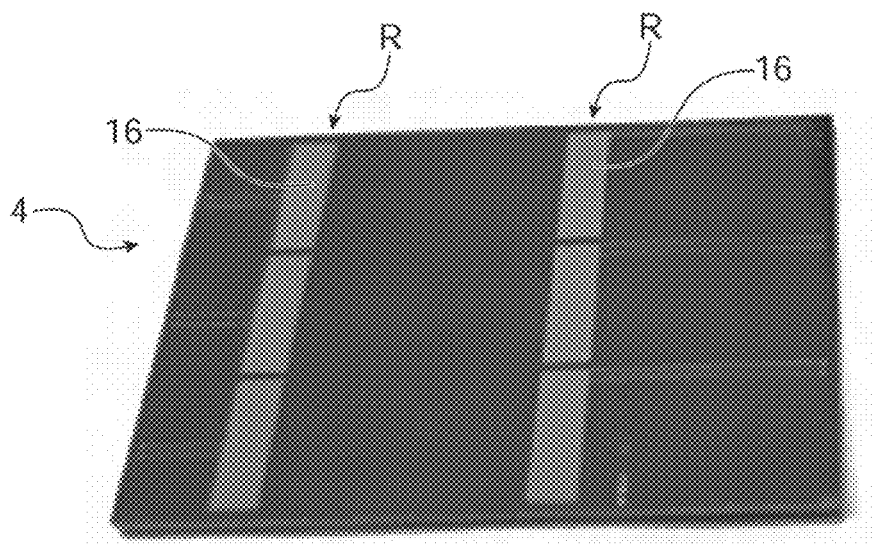
FIG. 5 is a perspective view of a plate used in the device of FIG. 1 showing the rows of actuators.

In FIG. 5, an example of plates with two rows R of piezoelectric actuators 16 can be seen. Each row includes three actuators and is situated at an antinode of the deflected shape or curves required. In this example the plate measures 30 mm long by 20 mm wide and the actuators are made from PZT.

A single actuator per row can be considered.

It is not required for the actuators to be positioned at each antinode of the deflected shape.

An example of a method for forming a scar using the device described above will now be described.

The case is considered where the plate 4 is immersed in a liquid (FIG. 9A).

The liquid Lq, for example a liquid adapted to the life of the cells C, is injected into the fluid cavity 3 immersing the plate 4. The liquid used forms a biological culture medium that is standard for the cell culture, for example it is DMEM Dulbecco/Vogt modified Eagle's minimal essential medium or RPMI 1640 (Roswell Park Memorial Institute medium 1640).

Next, the cells are injected into the liquid, for example by means of a pipette, and are distributed homogeneously in the liquid.

The control unit UC activates the actuators 16 in order to vibrate the plate 4 in the chosen mode and frequency, established previously in order to generate scars of the given width at one or more of the given locations. Activation of the actuators takes place during the sedimentation and before the adhesion of the cells to the accommodating surface. The actuators may be activated before the cells are injected.

The cells C are then distributed on top of the accommodating surface 8 and more particularly on top of the vibration antinodes of the plate 4 and move away from the vibration nodes. The cells sediment on the accommodating surface 8 and adhere thereto. In a variant, the actuators may be activated until all the cells are sedimented or be stopped during the sedimentation.

Figure 6A:
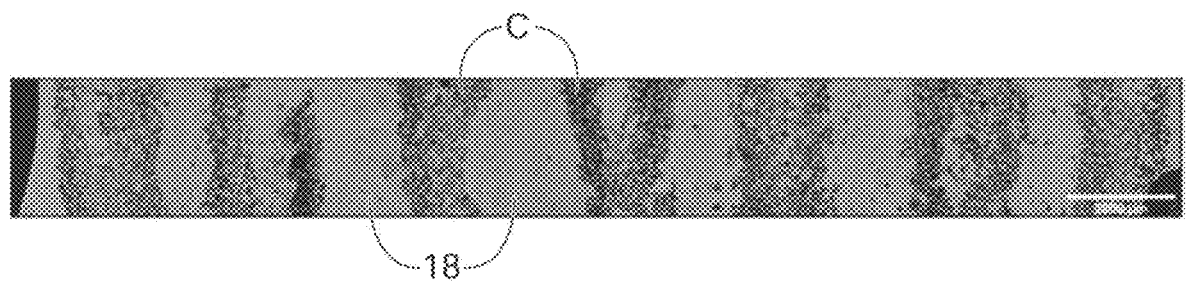
FIG. 6A is an image of the scars obtained by means of the locating device.

In FIG. 6A an example of distribution of cells obtained by means of the device according to the invention can be seen. In this example, seven scars 18 of average width 1787 µm are formed. The mean distance between the cells is 1380 µm.

Figure 6B:
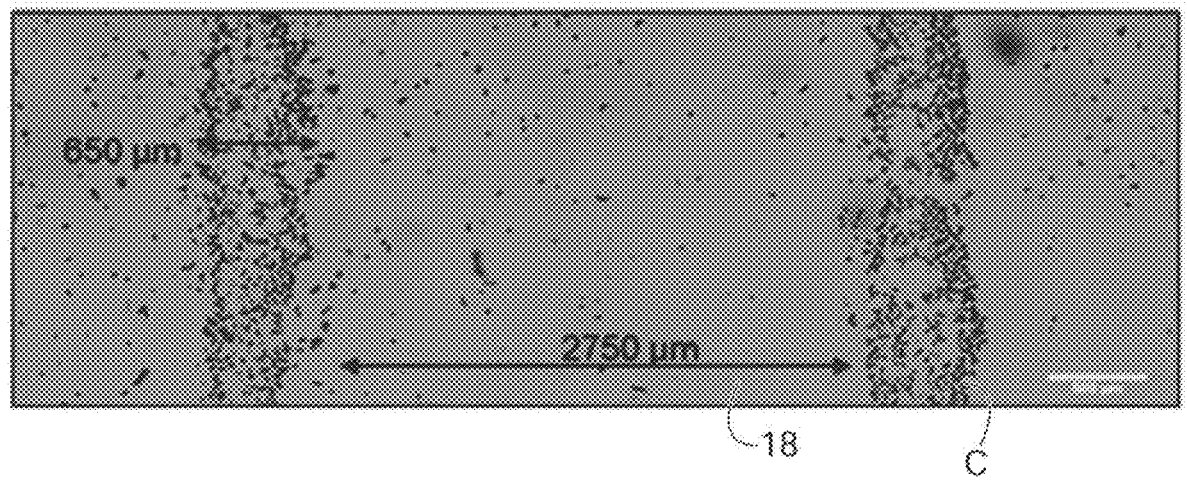
FIG. 6B is an image of other scars obtained by means of the locating device.

In FIG. 6B, another example of distribution obtained by means of the device can be seen. The scars 18 have a width of 2750 µm and the cells are distributed between the scars over a width of 650 µm.

A study of the migration of the cells can then be carried out. Advantageously, the housing and the plate are produced from optically transparent materials making it possible to view the cells when they migrate, for example by observation by means of a microscope. Photographs and/or a film can advantageously be produced during the migration.

The speed of migration depends on the cells and the substrate for scars with a width of 100 µm to 200 µm, the duration of the migration is around one day or even a few days.

According to a variant shown schematically in FIG. 9B, a volume G of liquid, for example of around 2 ml, is deposited solely on the plate 4 and the cells C are then injected into this volume of liquid. The volume may cover only part of the accommodating surface and therefore make it possible to limit the zone where the cells are located on the accommodating surface. The wettability of the accommodating surface of the plate is taken into account in order to be able to deposit a volume of liquid thereon.

The movement of the plate generates forces inside it.

Depositing the volume of liquid directly on the plate makes it possible to better control the plate where the cells are deposited. In the case of total immersion, the cells are deposited on the entire plate.

The external conditions for the migration may be modified, for example the temperature. The device may then include controllable heating means. Chemical species can be introduced at the same time as the cells.

By way of illustration, we shall give examples of sizing of the plates and of the actuators for producing scars around 100 µm to 2000 µm wide. A glass plate of 30×20 mm² is considered.

The scars form at the maximum movement of the vibrating structure and have a width of approximately ¼ of the wavelength defined by the characteristics of the plate and actuators.

By finite-element calculation, a modal analysis of the plate is carried out in order to obtain the deflected shape of the mode in question, for example the Lamb mode shown in FIG. 2A.

According to a first example, it is wished to generate scars around 2000 µm wide, this involves a deflected shape with a wavelength of approximately 8000 µm, approximately four periods on a plate 30 mm in length.

Each period makes 7500 µm. The zone corresponding to the maximum deformation of the plate, around a quarter of the period, has, for this mode at 175.4 kHz, a width of around 1875 µm, which is in accordance with the objective of a scar of approximately 2000 µm.

The actuators favoring this mode and the generation of scars of approximately 2000 µm will be positioned on zones of maximum movement of the plate. For example, a line of PZT actuators 16, around 1500 µm wide, positioned at 2600 µm from one edge of the plate and parallel thereto, and a second line of actuators 16 spaced apart from the first column of actuators, by one period, that is to say 7500 µm.

According to a second example, it is wished to form a scar with a width of less than 1000 µm, we can choose a mode with eight periods instead of four. The scar has a width of 937 µm.

It is then possible to position two lines of actuators 16 with a width of 750 µm, separated by one period, that is to say 3750 µm.

As mentioned above, actuators at each antinode are not required, this is shown by the above examples. A first example uses two lines of actuators whereas four antinodes are generated, and the second example uses two lines of actuators whereas eight antinodes are generated.

Figure 10:
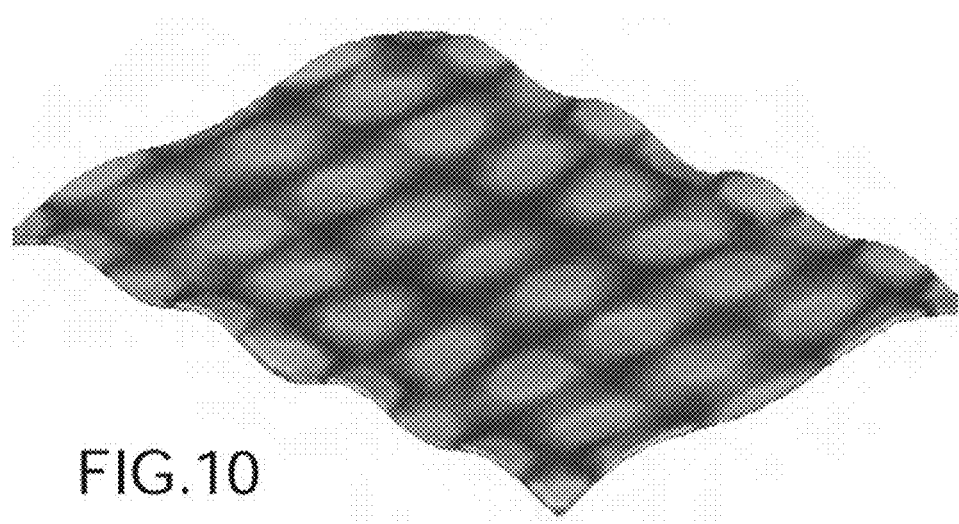
FIG. 10 is a representation of the deflected shape of a rectangular plate actuated in another stationary actuation mode.

Other ways of actuating the plate can be considered. For example, it is possible to choose an actuation mode in chequerboard form as shown in FIG. 10. In this case the actuators can be distributed so as to form a grid.

Any other form of plate can be considered, for example a beam shape, i.e. very long compared with the length thereof, or a disk shape.

Figure 3:
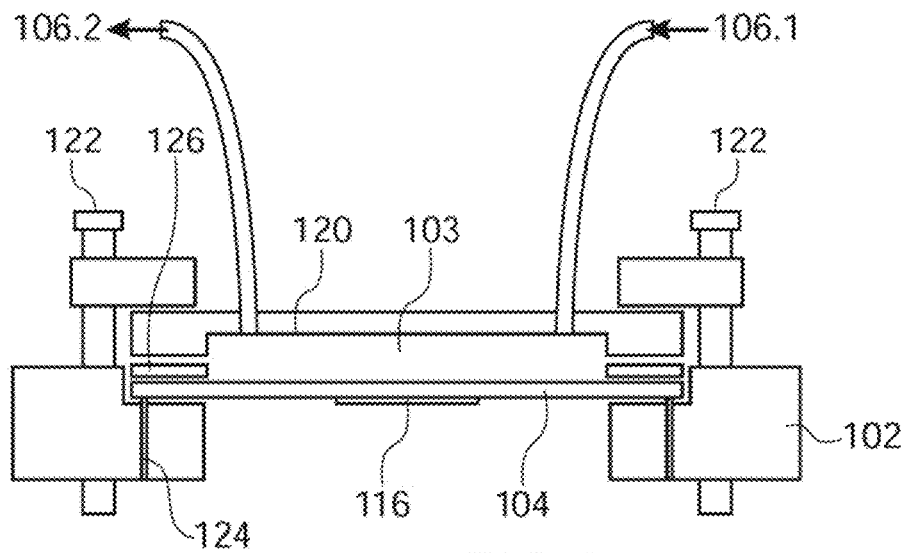
FIG. 3 is a side view of another example of a location device in which the plate is embedded.

According to a variant that is shown in FIG. 3, the plate 104 is embedded in the support. In this variant, the plate 104 is embedded between a support 102 and a cap 120. The plate 104 forms the bottom of the fluid cavity 103. In this variant, the cap 120 is fixed to the support 102 by screws 122. The fluid connections 106.1, 106.2 are effected in the cap.

The electrical connection 124 between the actuators 116 and the control unit UC is made through the support 102.

Advantageously, a seal 126 is interposed between the plate 104 and the cap 120.

Preferably, the cap and optionally the plate are transparent in order to allow in situ observation of the cells.

Figure 4A:
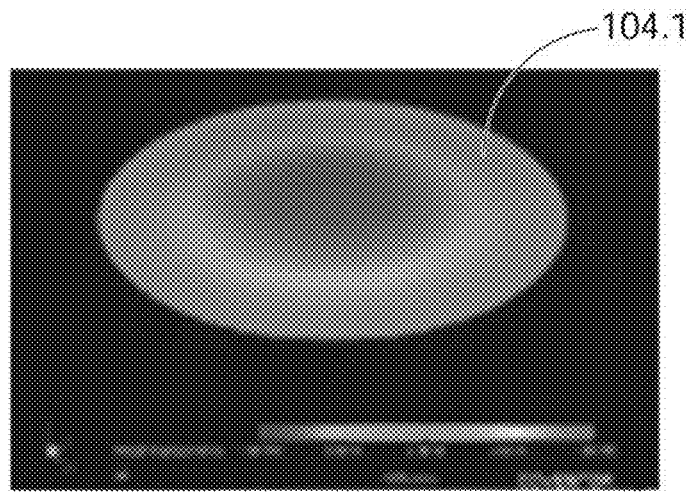
FIG. 4A is a representation of the deflected shape of an embedded circular plate actuated in a stationary mode.
Figure 4B:
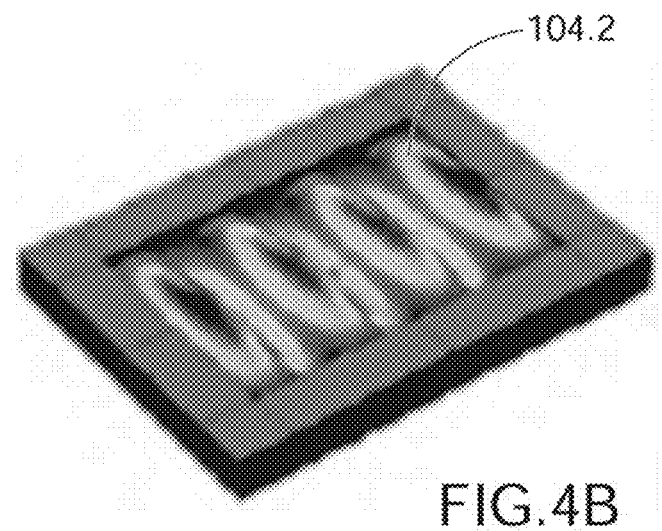
FIG. 4B is a representation of the deflected shape of an embedded rectangular plate actuated in a stationary mode.

In FIGS. 4A and 4B, representations can be seen of the deflected shape of the plates in the form of a disk 104.1 and rectangular in shape 104.2 embedded on the support. In the case of the rectangular plate 104.2, the antinode zones have a less uniform width over the entire width of the plate, compared with the plate 4 simply supported by the columns.

Figure 8:
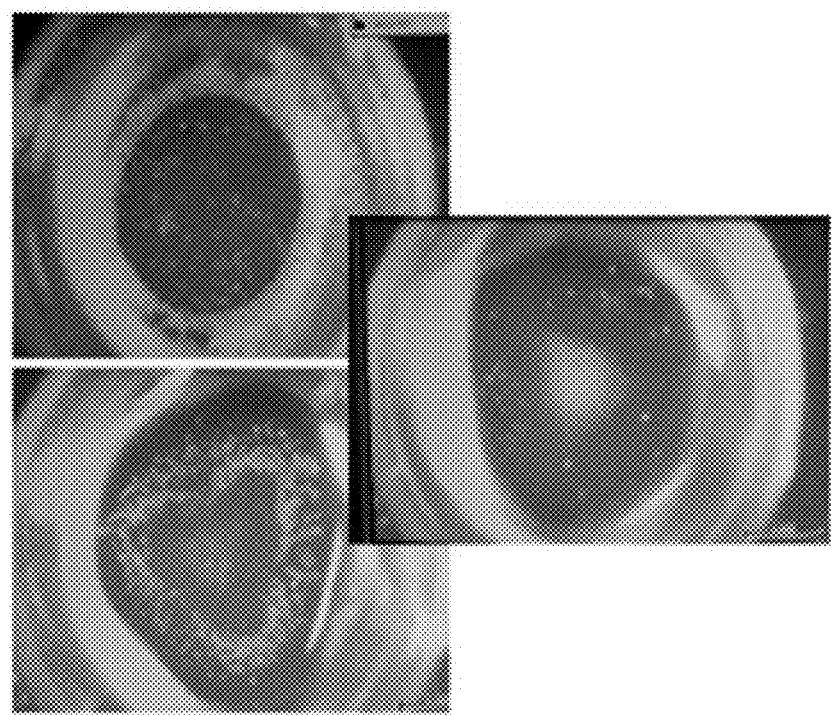
FIG. 8 shows various cell-location patterns obtained by the location device.

The device according to the invention makes it possible to locate the cells on a surface having adherent properties with respect to the cells in accordance with any pattern that can be obtained by plate actuation modes. In FIG. 8, examples can be seen of patterns of cells obtained by means of the device of the invention by the vibration of a plurality of resonant modes of a circular membrane. Such patterns make it possible to produce scars, or to locate cells at a given point for them to undergo one or more particular treatments with respect to other cells located at another point that undergo one or more other particular treatments or no treatment.

It can be considered locating various cells successively in accordance with different patterns by modifying the plate actuation modes. For example, the cells are injected successively into the fluid cavity, and at each injection the actuation mode is modified. The located deposits of cells made successively are possible since the migration of the cells is not an instantaneous phenomenon.

For example, the plate is made from silicon and the actuators are piezoelectric actuators made from AlN or PZT. In a variant, the plate is made from glass and the actuators are piezoelectric actuators, for example made from electroactive polymer, PZT or AlN.

The plate and the actuators are advantageously produced by microelectronic deposition and etching methods.

Figure 7A:
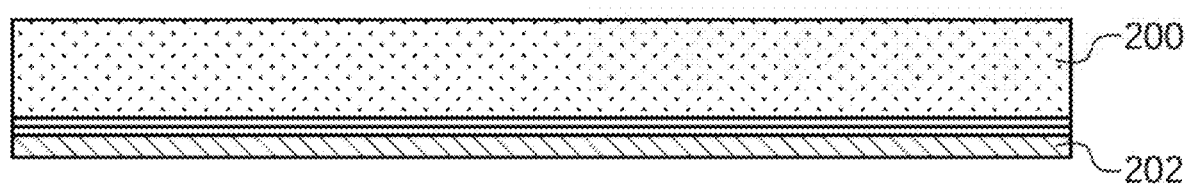
FIG. 7A to FIG. 7D are schematic representations of steps for manufacturing an example of a plate used in a locating device.

In FIGS. 7A to 7D, an example can be seen of a method for producing a glass plate carrying AlN actuators, comprising the steps that may be as follows:

Deposition of a layer of opaque material 202 on the rear face of the substrate 200. For example, the material used is titanium. A layer of titanium makes it possible to opacify the glass substrates and makes it possible to use these substrates on standard microelectronic equipment. The element thus obtained is shown in FIG. 7A.

Figure 7B:
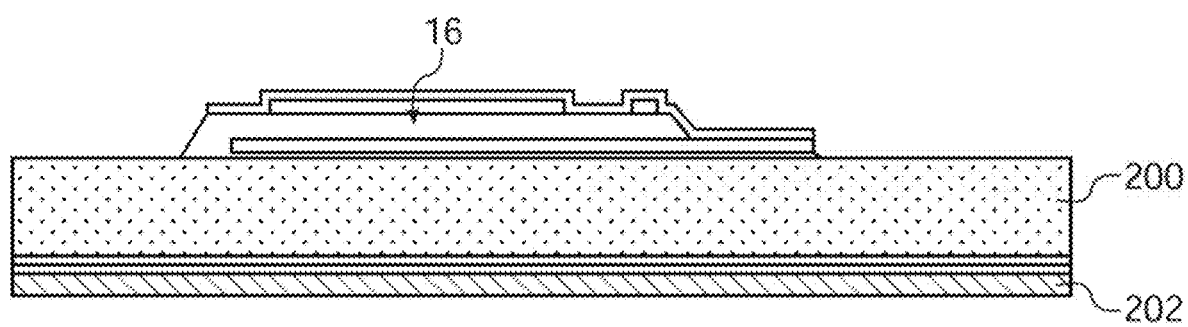

Formation of the piezoelectric actuators 16 on the front face, for example by deposition and etching, the actuators comprising a layer of AlN between two electrodes. The element thus obtained is shown in FIG. 7B.

Figure 7C:
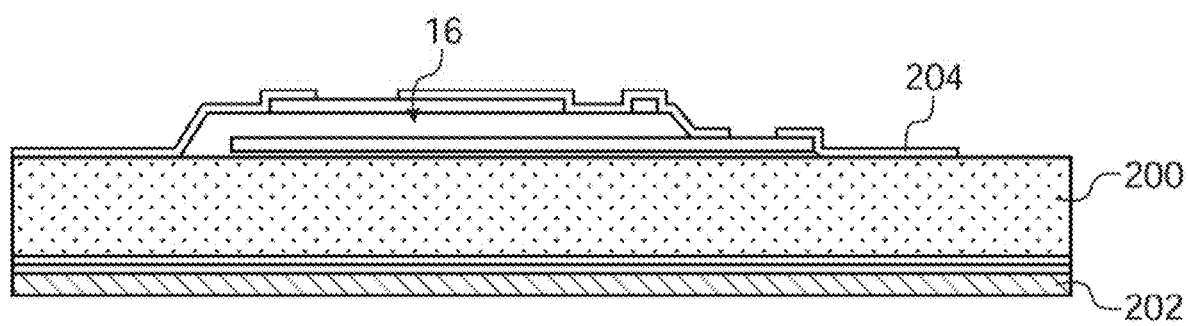
Figure 7D:
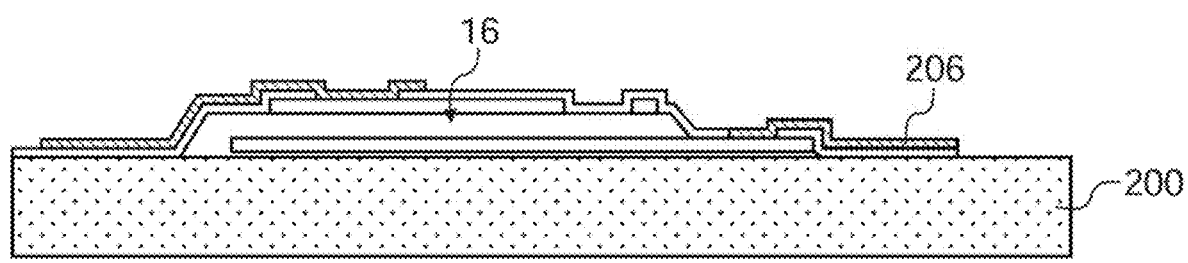

Formation of a passivation layer 204 on the actuators, for example by deposition. The passivation layer is next etched locally in order to reach the electrodes with a view to the formation of the electrical contacts. The element thus obtained is shown in FIG. 7C.

Formation of the electrical contacts 206 in order to connect the actuators to the control unit. The electrical contacts are formed using a mask, by depositing a metal layer, for example gold, and by etching this layer.

Removal of the opaque layer, for example by etching. The element thus obtained in shown in FIG. 7D.

A layer insulating the contacts from the liquid is formed, this is for example a layer of insulating polymer, for example produced by deposition.

The plate can then be disposed in the fluid cavity, for example on the columns, and be connected to the control unit.

The device according to the invention therefore makes it possible to generate temporary cell exclusion zones adapted for the study of cell migrations.

The location thus obtained is controlled and repeatable. It is independent of the level of technical skill of the operator, who previously used a stylus or a scalpel to form the scars, and it does not use any chemical treatments that could influence the cell migration. The location device is advantageously compatible with the culture of mammal cells. This system is particularly adapted to the quantification of the impact of therapeutic molecules targeting the cytoskeleton for inhibiting metastatic invasion in cancer.

According to another application, the invention makes it possible to locate the development of bacteria or foams so as to leave transparent the scanning zone of the immersed optical sensors or of an immersed laser teledetection device of the LIDAR (light detection and ranging) type.

The invention claimed is:

1. A device for locating biological objects on an accommodating surface, the device comprising:
   a fluid cavity within a housing;
   at least one fluid connector configured to introduce liquid and biological objects into the fluid cavity;
   a plate provided with said accommodating surface having properties of adhesion vis-à-vis biological objects, said plate being suspended in the fluid cavity;
   at least one actuator for vibrating the plate in at least one stationary mode, said at least one actuator being configured to act on the plate; and
   a control unit configured to control the at least one actuator so that the plate vibrates in a stationary mode with a wavelength $\lambda$ of between 3 times and 20 times a size of the biological objects,
   wherein a bottom surface of the plate is supported by a support structure, the support structure includes a plurality of columns and the plate is supported on free ends of the plurality of columns.

2. The location device according to claim 1, wherein said at least one actuator is disposed with respect to the plate at an antinode of a deflected shape of the plate in stationary mode.

3. The location device according to claim 1, wherein the plurality of columns extend between a bottom surface of the housing and the bottom surface of the plate.

4. The location device according to claim 3, wherein the columns are in contact with the plate at at least some nodes of a deflected shape of the plate in said stationary mode.

5. The location device according to claim 1, wherein the at least one actuator is a piezoelectric actuator fixed to the plate.

6. The location device according to claim 1, wherein at least part of the fluid cavity is optically transparent.

7. A system for studying migration of cells including a location device according to claim 6, and a device for observing the biological objects on the plate.

8. A method for locating biological objects in a given pattern using a device according to claim 1, including:
   placing liquid in the fluid cavity at least over part of the accommodating surface,
   injecting biological objects into said liquid,
   activation of the at least one actuator so that the plate vibrates in a stationary mode chosen so as to obtain the given pattern,
   sedimentation of the biological objects on the accommodating surface in the given pattern, and
   stoppage of the at least one actuator during or after the sedimentation.

9. The location method according to claim 8, wherein the liquid surrounds the plate.

10. The location method according to claim 8, wherein the liquid is deposited solely on the accommodating surface.

11. A method for locating biological objects in a given pattern using a device and analyzing migration of biological cells, the biological objects being cells, the device including a fluid cavity within a housing; at least one fluid connector configured to introduce liquid and biological objects into the fluid cavity; a plate provided with an accommodating surface having properties of adhesion vis-à-vis biological objects, said plate being suspended in the fluid cavity; at least one actuator for vibrating the plate in at least one stationary mode, said at least one actuator being configured to act on the plate; and a control unit configured to control the at least one actuator so that the plate vibrates in a stationary mode with a wavelength $\lambda$ of between 3 times and 20 times a size of the biological objects, said method comprising:

placing liquid in the fluid cavity at least over part of the accommodating surface;
  injecting biological objects into said liquid;
  activation of the at least one actuator so that the plate vibrates in a stationary mode chosen so as to obtain the given pattern;
  sedimentation of the biological objects on the accommodating surface in the given pattern;
  stoppage of the at least one actuator during or after the sedimentation; and
  after the sedimentation of biological cells on the accommodating surface form at least one scar, observing the migration of the biological cells.

12. The method according to claim 11, wherein said at least one actuator is disposed with respect to the plate at an antinode of a deflected shape of the plate in stationary mode.

13. The method according to claim 11, wherein a bottom surface of the plate is supported by a support structure, the support structure includes a plurality of columns and the plate is supported on free ends of the plurality of columns, and wherein the plurality of columns extend between a bottom surface of the housing to the bottom surface of the plate.

14. The method according to claim 13, wherein the supports are in contact with the plate at at least some nodes of a deflected shape of the plate in said stationary mode.

15. The method according to claim 11, wherein the at least one actuator is a piezoelectric actuator fixed to the plate.

16. The method according to claim 11, wherein at least part of the fluid cavity is optically transparent.

17. The method according to claim 11, wherein the liquid surrounds the plate.

* * * * *